US00PP23915P2

(12) United States Plant Patent
Smaal et al.

(10) Patent No.: US PP23,915 P2
(45) Date of Patent: Sep. 24, 2013

(54) RASPBERRY PLANT NAMED 'ADVABEREEN'

(50) Latin Name: *Rubus idaeus*
Varietal Denomination: Advabereen

(75) Inventors: André Smaal, De Kwakel (NL); Gerrit de Weert, Rossum (NL)

(73) Assignee: Advanced Berry Breeding, De Kwakel (NL)

( * ) Notice: Subject to any disclaimer, the term of this patent is extended or adjusted under 35 U.S.C. 154(b) by 0 days.

(21) Appl. No.: 13/385,280

(22) Filed: Feb. 10, 2012

(51) Int. Cl.
*A01H 5/00* (2006.01)

(52) U.S. Cl.
USPC ..... Plt./204

(58) Field of Classification Search
USPC ..... Plt./204
See application file for complete search history.

*Primary Examiner* — Kent L Bell
(74) *Attorney, Agent, or Firm* — C. A. Whealy

(57) ABSTRACT

A new and distinct cultivar of Raspberry plant named 'Advabereen', characterized by its upright and somewhat bushy plant habit; freely branching habit; high fruit production; uniform fruit ripening; large firm bright red-colored fruits; pleasant and sweet fruit taste; and good fruit postharvest longevity.

2 Drawing Sheets

Botanical designation: *Rubus idaeus.*
Cultivar denomination: 'ADVABEREEN'.

BACKGROUND OF THE INVENTION

The present Invention relates to a new and distinct cultivar of Raspberry plant, botanically known as *Rubus idaeus* and hereinafter referred to by the name 'Advabereen'.

The new Raspberry plant is a product of a planned breeding program conducted by the Inventors in Rossum, Gelderland, The Netherlands. The objective of the breeding program was to develop new Raspberry plants with good fruit quality, productivity and uniformity.

The new Raspberry plant originated from a cross-pollination made by the Inventors during the spring of 2007 of a proprietary Raspberry selection identified as code number 207005, not patented, as the female, or seed, parent with a proprietary Raspberry selection identified as code number 207126, not patented, as the male, or pollen, parent. The new Raspberry plant was discovered and selected by the Inventors as a single plant from within the progeny of the stated cross-pollination in a controlled environment in Rossum, Gelderland, The Netherlands in September, 2008.

Asexual reproduction of the new Raspberry plant by root cuttings in a controlled environment at Rossum, Gelderland, The Netherlands since the spring of 2009 has shown that the unique features of this new Raspberry plant are stable and reproduced true to type in successive generations of asexual reproduction.

SUMMARY OF THE INVENTION

Plants of the new Raspberry have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Advabereen'.

These characteristics in combination distinguish 'Advabereen' as a new and distinct Raspberry plant:

1. Upright and somewhat bushy plant habit.
2. Freely branching habit.
3. High fruit production.
4. Uniform fruit ripening.
5. Large firm bright red-colored fruits.
6. Pleasant and sweet fruit taste.
7. Good fruit postharvest longevity.

Plants of the new Raspberry differ from plants of the female parent selection in the following characteristics:

1. Plants of the new Raspberry produce larger fruits than plants of female parent selection.
2. Fruits of plants of the new Raspberry do not become darker in color after harvest whereas fruits of plants of the female parent selection become darker in color after harvest.

Plants of the new Raspberry differ primarily from plants of the male parent selection in the fruit color as fruits of plants of the new Raspberry are lighter in color than fruits of the male parent selection.

Plants of the new Raspberry can be compared to plants of Raspberry 'Polka', not patented. In side-by-side comparisons conducted in Rossum, Gelderland, The Netherlands, plants of the new Raspberry differed from plants of 'Polka' in the following characteristics:

1. Plants of the new Raspberry were more freely branching than plants of 'Polka'.
2. Plants of the new Raspberry had smaller thorns than plants of 'Polka'.
3. Plants of the new Raspberry required less vernalization than plants of 'Polka'.
4. Fruits of plants of the new Raspberry were lighter in color than fruits of plants of 'Polka'.
5. Fruits of plants of the new Raspberry did not become darker in color after harvest whereas fruits of plants of 'Polka' became darker in color after harvest.

BRIEF DESCRIPTION OF THE PHOTOGRAPHS

The accompanying colored photographs illustrate the overall appearance of the new Raspberry plant showing the colors as true as it is reasonably possible to obtain in colored reproductions of this type. Colors in the photographs may differ slightly from the color values cited in the detailed botanical description which accurately describe the colors of the new Raspberry plant.

The photographs on the first sheet are side perspective views of typical fruiting plants of 'Advabereen'.

The photographs on the second sheet are close-up views of typical fruits of 'Advabereen'.

DETAILED BOTANICAL DESCRIPTION

The aforementioned photographs, following observations and measurements describe plants grown during the summer and autumn in 10-liter containers in an outdoor nursery in De Kwakel, The Netherlands and under typical commercial production practices. During the production of the plants, day temperatures averaged 17° C. and night temperatures averaged 15° C. Plants were one year old when the photographs and description were taken. In the following description, color references are made to The Royal Horticultural Society Colour Chart, 1995 Edition, except where general terms of ordinary dictionary significance are used.

Botanical classification: *Rubus idaeus* 'Advabereen'.

Parentage:

*Female, or seed, parent*.—Proprietary seedling selection of *Rubus idaeus* identified as code number 207005, not patented.

*Male, or pollen, parent*.—Proprietary seedling selection of *Rubus idaeus* identified as code number 207126, not patented.

Propagation:

*Type*.—By root cuttings.

*Time to initiate roots*.—About 12 to 14 days at 15° C. to 17° C.

*Time to produce a rooted young plant*.—About six weeks at 15° C. to 17° C.

*Root description*.—Medium to thin in thickness, fibrous; brownish white in color.

*Rooting habit*.—Freely branching; dense.

Plant description:

*Plant and growth habit*.—Upright and somewhat bushy plant habit; vigorous growth habit; rapid growth rate.

*Plant height*.—About 180 cm to 200 cm.

*Plant diameter*.—About 40 cm.

Lateral branch description:

*Branching habit*.—Freely branching habit with about seven to eight lateral branches developing per plant.

*Length*.—About 50 cm.

*Diameter*.—About 8 mm.

*Internode length*.—About 7 cm.

*Strength*.—Strong.

*Aspect*.—Mostly erect.

*Texture*.—Smooth, glabrous.

*Color, developing*.—Close to 145B.

*Color, developed*.—Close to 182B.

*Thorns*.—Density: About five per linear cm. Length: About 1 mm. Width: About 1 mm. Shape: Roughly deltoid. Apex: Acuminate. Base: Truncate. Margin: Entire. Color, immature: Close to 144D. Color, mature: Close to 144D; apex, close to 184B.

Leaf description:

*Arrangement*.—Alternate; compound with typically three leaflets.

*Leaf length*.—About 14 cm.

*Leaflet length*.—About 10 cm.

*Leaf width*.—About 15 cm.

*Leaflet width*.—About 7 cm.

*Leaflet shape*.—Ovate.

*Leaflet apex*.—Cuspidate.

*Leaflet base*.—Cordate to cuneate.

*Leaflet margin*.—Double serrate.

*Leaflet texture, upper and lower surfaces*.—Slightly rippled, glabrous.

*Leaflet venation*.—Pinnate.

*Leaflet color*.—Developing leaflets, upper surface: Close to 144A. Developing leaflets, lower surface: Close to 194B. Fully expanded leaflets, upper surface: Close to 143B; venation, close to 144A. Fully expanded leaflets, lower surface: Close to 194B; venation, close to 147D.

*Petioles*.—Length, leaf: About 6 cm to 7 cm. Length, leaflet: About 3 cm. Diameter, leaf: About 3 mm. Diameter, leaflet: About 3 mm. Texture, upper and lower surfaces: Sparsely prickled. Color, upper and lower surfaces: Close to 145B.

Flower description:

*Flower form and flowering habit*.—Single star-shaped flowers arranged in sprays at lateral apices; freely flowering with about two to six flowers per spray; flowers face mostly outwardly.

*Fragrance*.—None detected.

*Natural flowering season*.—Plants flower during the spring and early autumn in The Netherlands.

*Flower buds*.—Length: About 5 mm to 10 mm. Diameter: About 5 mm to 10 mm. Shape: Roughly deltoid. Color: Close to 141D.

*Flower diameter*.—About 2.5 cm.

*Flower depth* (*height*).—About 7 mm.

*Petals*.—Arrangement: Single whorl of five petals. Length: About 1.5 cm. Width: About 3 mm to 5 mm. Shape: Lanceolate to narrowly ovate. Apex: Obtuse. Base: Attenuate. Margin: Entire. Texture, upper and lower surfaces: Smooth, glabrous. Color: When opening and fully opened, upper surface: Close to 155D. When opening and fully opened, lower surface: Close to 155D.

*Sepals*.—Arrangement: Single whorl of five sepals. Length: About 2 cm. Width, at the base: About 2 cm. Shape: Deltoid. Apex: Acuminate. Margin: Entire. Texture, upper and lower surfaces: Slightly pubescent. Color, upper and lower surfaces: Close to 145B.

*Peduncles*.—Length: About 5 cm to 10 cm. Diameter: About 1.5 mm. Strength: Strong. Texture: Prickled. Color: Close to 145A.

*Pedicels*.—Length: About 3 cm to 5 cm. Diameter: About 1.5 mm. Strength: Strong. Texture: Prickled. Color: Close to 145B.

*Reproductive organs*.—Stamens: Quantity per flower: About 50. Filament color: Close to 155D. Anther length: About 1 mm. Anther color: Close to 164C and 156C. Pollen color: Close to 196C. Pistils: Quantity per flower: About 50. Stigma shape: Rounded. Stigma color: Close to 155D. Style length: About 5 mm. Style color: Close to 155D. Ovary color: Close to 155D. Receptacle: Height: About 1 cm. Diameter: About 1 cm. Shape: Conical. Color: Close to 155D. Fruits (aggregate of drupelets): Quantity: One per flower.

Number of drupelets per fruit: About 100. Length: About 2.5 cm. Diameter: About 2.3 cm to 2.5 cm. Shape: Broadly conical; somewhat irregular drupelet arrangement. Weight: About 5 gr. Firmness: Firm. Taste: Pleasant, sweet. Luster: Glossy. Postharvest longevity: Good postharvest longevity, fruits last up to ten days; fruits do not become darker after harvest. Color: Close to 43B. Seeds: Quantity: One per drupelet. Length: About 2.5 mm. Diameter: About 1 mm. Texture: Smooth, glabrous. Color: Close to 20D.

Disease & pest resistance: Plants of the new Raspberry have not been noted to be resistant to pathogens and pests common to Raspberry plants.

Temperature tolerance: Plants of the new Raspberry have been observed to tolerate temperatures ranging from 4° C. to 35° C.

It is claimed:

1. A new and distinct Raspberry plant named 'Advabereen' as illustrated and described.

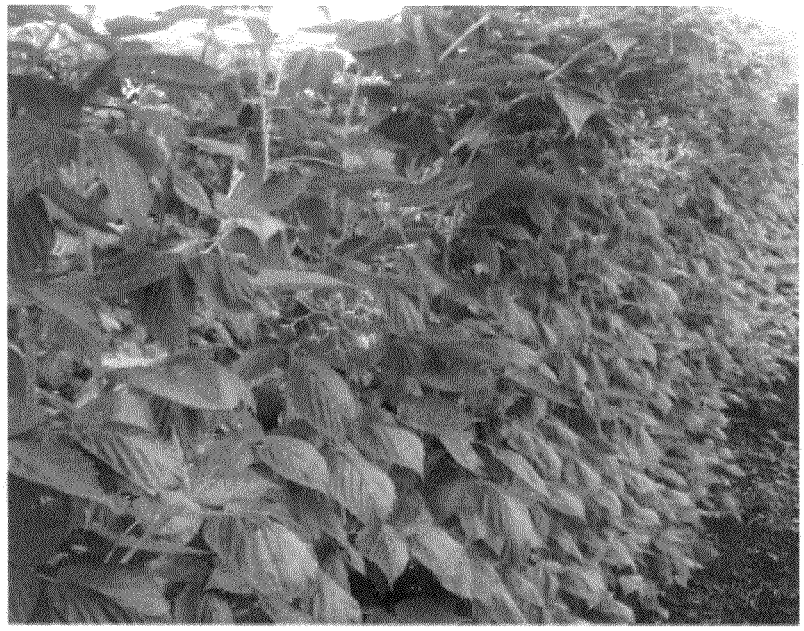
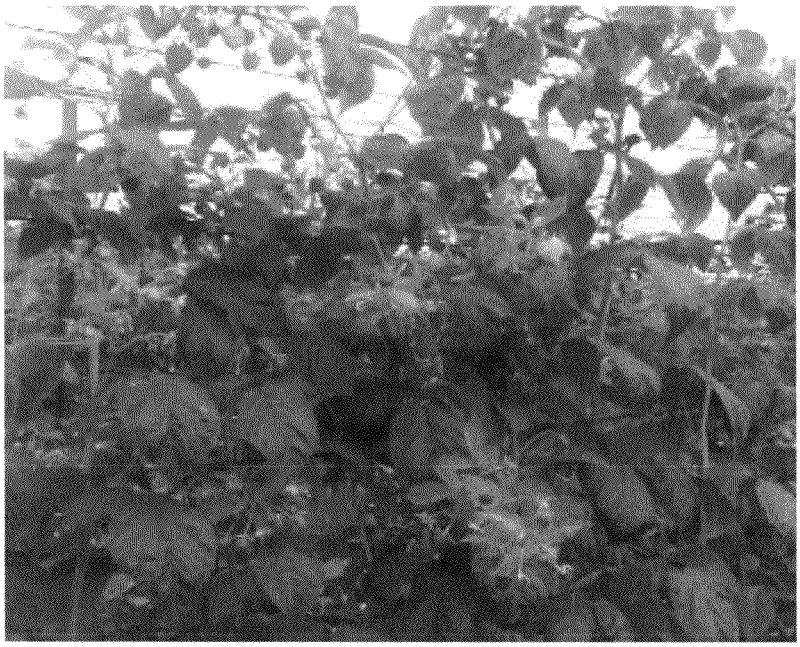

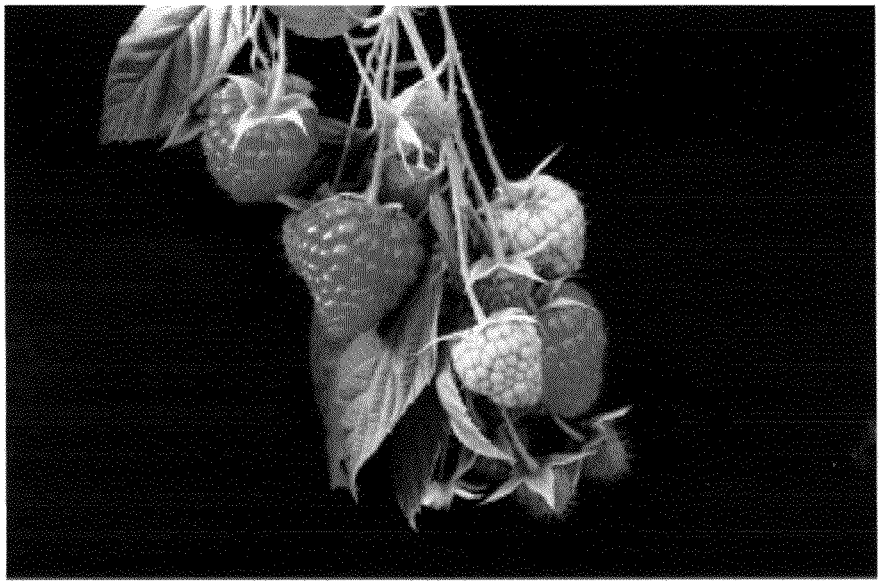
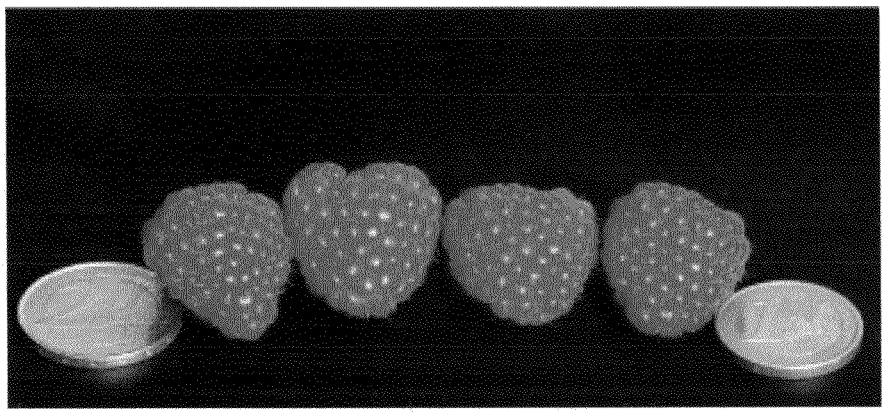

* * * * *